United States Patent [19]

Plath et al.

[11] 4,255,587

[45] Mar. 10, 1981

[54] N-SUBSTITUTED 2,6-DIALKYLANILINES AND PROCESS FOR THEIR PREPARATION

[75] Inventors: Peter Plath, Ludwigshafen; Wolfgang Rohr, Mannheim; Norbert Goetz, Worms, all of Fed. Rep. of Germany

[73] Assignee: BASF Aktiengesellschaft, Fed. Rep. of Germany

[21] Appl. No.: 2,328

[22] Filed: Jan. 10, 1979

[30] Foreign Application Priority Data

Jan. 19, 1978 [DE] Fed. Rep. of Germany ... 2802211

[51] Int. Cl.$^3$ .......................................... C07C 101/44
[52] U.S. Cl. .................... 560/43; 260/340.7; 260/340.9 R; 560/44; 71/88; 71/111; 71/112
[58] Field of Search ................. 260/340.9, 340.7; 560/43

[56] References Cited

U.S. PATENT DOCUMENTS

| | | | |
|---|---|---|---|
| 2,533,723 | 12/1950 | Dombrow | 260/577 |
| 3,542,850 | 11/1970 | Jansen et al. | 560/43 |
| 3,882,162 | 5/1975 | Clayton | 560/43 |
| 3,905,987 | 9/1975 | Booher | 260/340.7 |
| 4,025,648 | 5/1977 | Hubele | 424/309 |
| 4,032,657 | 6/1977 | Moser | 424/309 |
| 4,046,911 | 9/1977 | Hubele | 424/285 |
| 4,093,738 | 6/1978 | Hubele | 424/309 |

FOREIGN PATENT DOCUMENTS

| | | |
|---|---|---|
| 2350944 | 4/1974 | Fed. Rep. of Germany ............. 560/43 |
| 2513788 | 10/1975 | Fed. Rep. of Germany . |
| 2802211 | 7/1979 | Fed. Rep. of Germany ............. 560/43 |
| 1500581 | 2/1978 | United Kingdom . |

OTHER PUBLICATIONS

Mueller et al., Journ. Amer. Chem. Soc., 65, p. 1017 (Jun., 1943).
Chem. Abstracts 77: 19275e.
Chem. Abstracts 77: 101030e.
Chem. Abstracts 86: 72075b.
J. Chem. Soc. (1961), pp. 3303–3308.
Chemische Berichte, 22 (1889), pp. 1792–1795.
C. R. Acad. Sc. Paris 264 (Series C, 1967), pp. 1864–1865.
J. Am. Chem. Soc. 65 (1943), pp. 1017–1018.
Houben-Weyl Methoden der Organischen Chemie, 11 (1), p. 275.
Houben-Weyl, Methoden der Organischen Chemie, 4 (2), pp. 180–183.
Journ. Applied Chem. 5 (1955), pp. 289–296.

*Primary Examiner*—Ethel G. Love
*Attorney, Agent, or Firm*—Keil & Witherspoon

[57] ABSTRACT

Novel N-substituted 2,6-dialkylanilines and process for the preparation of N-substituted 2,6-dialkylanilines by reaction of 2,6-dialkylanilines with carbonyl compounds, followed by catalytic hydrogenation with hydrogen. The products are starting materials for the preparation of dyes and pesticides.

9 Claims, No Drawings

N-SUBSTITUTED 2,6-DIALKYLANILINES AND PROCESS FOR THEIR PREPARATION

The present invention relates to novel N-substituted 2,6-dialkylanilines and a process for the preparation of N-substituted 2,6-dialkylanilines by reaction of 2,6-dialkylanilines with carbonyl compounds, followed by catalytic hydrogenation with hydrogen.

J. Chem. Soc. (1961), 3,303–3,308 discloses that 2,6-dimethylaniline and ethyl α-bromopropionate can be reacted in benzene to give ethyl α-(2,6-dimethylanilino)propionate. Though the reaction time is 96 hours, the yield achievable is only 37 percent. As is shown, however, in Chemische Berichte, 22 (1889), 1,792–1,795, the yield is virtually quantitative if the two sterically hindering substituents in the 2,6-position are absent, ie. if aniline is used as the starting material. A comparison of the reaction of aniline and of ortho-methylaniline with ethyl 2-chloropropionate for 12 hours at 120°–125° C. in the presence of sodium acetate (C.R. Acad. Sc. Paris, 264 (Series C, 1967), 1,864–1,865) shows a yield of 40 percent based on aniline and 20 percent based on ortho-methylaniline, and thus shows the effect of even one ortho-substituent. The same reaction with the methyl group in the meta-position or para-position instead of the ortho-position gives yields of 33 and 57 percent. Accordingly, the yield increases the more remote the substituent is from the amino group.

If 6 moles of 2,6-dimethylaniline are reacted with 18 moles of methyl α-bromopropionate in the presence of 6.6 moles of sodium bicarbonate, the yield, according to German Laid-Open Application DOS No. 2,350,944 (page 15, Example 1) increases to 79.6 percent; the total reaction time is more than 19 hours.

All these processes are unsatisfactory in respect of simple and economical operation, and in respect of yield and of the working up of the end product.

We have found that an N-substituted 2,6-dialkylaniline of the formula

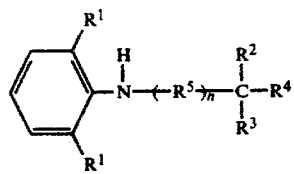

where the individual radicals $R^1$, $R^2$ and $R^3$ may be identical or different and each is an aliphatic radical, $R^2$ may also be hydrogen,

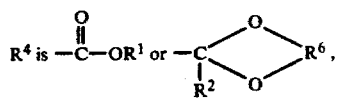

where $R^1$ and $R^2$ have the above meanings and $R^6$ is an aliphatic radical, and $R^3$ may also be hydrogen if $R^4$ is

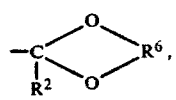

$R^5$ is an aliphatic radical and n is 0 or an integer, is obtained in an advantageous manner by reaction of an aromatic amine with a carbonyl compound and hydrogenation of the resulting Schiff base if a 2,6-dialkylaniline of the formula

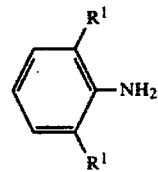

where $R^1$ has the above meaning is reacted with a carbonyl compound of the formula

where $R^3$ and $R^4$ have the above meanings and $R^7$ together with the adjacent carbon atom is

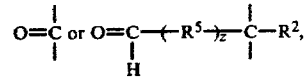

where $R^2$ and $R^5$ have the above meanings and z is 0 or an integer, and, in a second step, the resulting Schiff base is hydrogenated with hydrogen in the presence of a hydrogenation catalyst.

Further, we have found the novel N-substituted 2,6-dialkylanilines of the formula

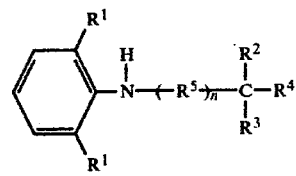

where the individual radicals $R^1$, $R^2$ and $R^3$ may be identical or different and each is an aliphatic radical, $R^2$ may also be hydrogen,

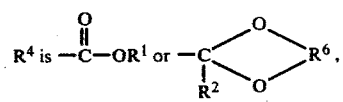

where $R^1$ and $R^2$ have the above meanings and $R^6$ is an aliphatic radical, and $R^3$ may also be hydrogen if $R^4$ is

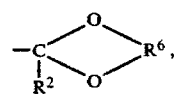

$R^5$ is an aliphatic radical and n is 0 or an integer, and, if both radicals $R^1$ are methyl, ethyl or isopropyl or one radical $R^1$ is methyl and the other radical $R^1$ is ethyl, isopropyl or sec.-butyl, and if at the same time n is 0 and $R^2$ is hydrogen and $R^4$ is

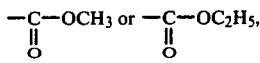

$R^3$ is an aliphatic radical of 2 or more carbon atoms or is methyl substituted by a substituent bonded to the carbon via a hetero-atom.

Where 2,6-dimethylaniline and methyl pyruvate are used, the reaction may be represented by the following equations:

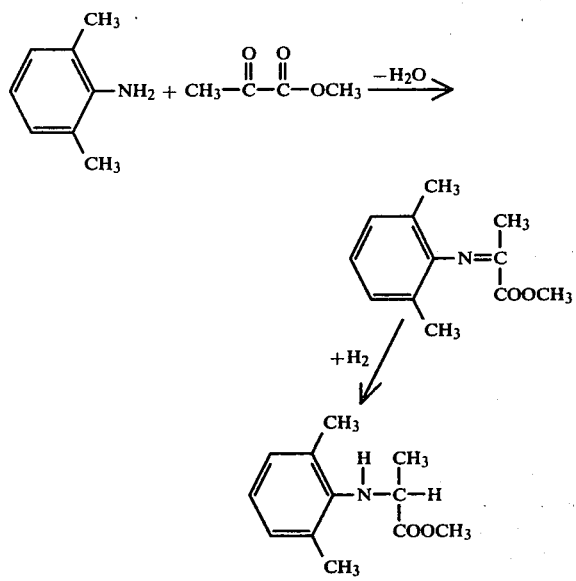

Compared to the conventional processes, the process according to the invention gives N-substituted 2,6-dialkylanilines more simply and more economically, and in better yield and greater purity. Since neither a hydrogen halide is formed nor a basic compound is added to bind such a halide, the process is simpler to operate and the effluent problems which arise in conventional processes, particularly on an industrial scale, because of the large amounts of salt formed, are avoided. Environmentally, the process is thus more advantageous. Since both stages of the reaction take place rapidly, the reaction time of both stages together is relatively shorter and hence the overall spacetime yield is better. The process can advantageously be carried out as a one-vessel operation.

All these advantageous results are surprising in view of the prior art. Since two sterically hindering substituents are present, in the 2-position and 6-position, it would have been expected that the condensation and hydrogenation would have been made difficult or impossible. Thus, J. Am. Chem. Soc., 65 (1943), 1,017 and 1,018 shows that even 2-naphthylamine, which is unsubstituted in the two ortho-positions, when reacted with ethyl oxaloacetate, gives only a 41 percent yield of the Schiff base diethyl-2-naphthyliminosuccinate; the reaction time is 48 hours. The end product was recrystallized twice from ethanol before being hydrogenated, in a separate reaction, to give diethyl 2-naphthylaminosuccinate. Since, in the process according to the invention, the Schiff base is in general not purified but instead is reacted by a one-vessel process, with or without a change of solvent between the first and the second stage, the high yield of pure end product is also surprising in the light of the above publication. Bearing in mind the behavior of anilines when reacted with acrylonitrile, it would also have been expected that, at the very least, the yield of the end products according to the invention would be low, since unsubstituted aniline (Houben-Weyl, Methoden der Organischen Chemie, Volume 11/1, page 275) gives a 53.4 percent yield of β-anilinopropionitrile, whilst anilines substituted in both ortho-positions do not react at all with acrylonitrile.

The starting material III can be reacted with the starting material II in stoichiometric amount or using an excess of either component relative to the other, advantageously in an amount of from 0.8 to 2, preferably from 1 to 1.2, moles of starting material III per mole of starting material II. Preferred starting materials II and III and accordingly preferred end products I are those where the individual radicals $R^1$, $R^2$ and $R^3$ are identical or different and each is alkyl of 1 to 7, preferably of 1 to 4, carbon atoms; $R^3$ can also be

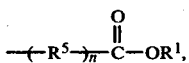

where $R^1$ has the above meaning and n and $R^5$ the preferred meanings given below, $R^2$ may also be hydrogen, $R^4$ is

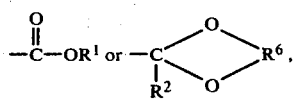

where $R^1$ and $R^2$ have the above meanings and $R^6$ is alkylene of 2 or 3 carbon atoms, $R^3$ may also be hydrogen if $R^4$ is

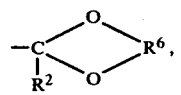

$R^5$ is alkylene of 1 to 3 carbon atoms and n and z may be identical or different and each is 0, 1, 2 or 3, and $R^7$ together with the adjacent carbon is

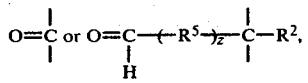

where $R^2$, $R^5$ and z have the above preferred meanings. If $R^7$ is oxo, $R^2$ is hydrogen and n and z are 0; if $R^7$ together with the adjacent carbon is

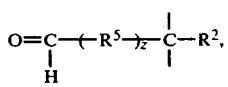

then if n is 1, z is 0, and if n is >1, z is n −1. If the end product I contains 3 or 4 radicals $R^1$ and/or 2 radicals $R^2$, the individual radicals $R^1$ and $R^2$ may be identical or different. The above radicals may in addition be substituted by groups which are inert under the reaction conditions, for example alkyl of 1 to 4 carbon atoms.

Examples of suitable starting materials II are 2,6-dimethyl-, 2,6-diethyl-, 2,6-di-n-propyl-, 2,6-diisopropyl, 2,6-di-n-butyl-, 2,6-diisobutyl-, 2,6-di-sec.-butyl-, 2,6-di-tert.-butyl-, 2-methyl-6-ethyl-, 2-methyl-6-propyl-, 2-methyl-6-isopropyl-, 2-methyl-6-butyl-, 2-methyl-6-isobutyl-, 2-methyl-6-sec.-butyl-, 2-methyl-6-tert.-butyl-, 2-ethyl-6-propyl-, 2-ethyl-6-isopropyl-, 2-ethyl-6-butyl-, 2-ethyl-6-isobutyl- and 2-ethyl-6-tert.-butyl-aniline.

Suitable starting materials III include methyl 2-oxopropionate, 2-oxobutyrate, 2-oxovalerate, 2-oxocaproate and 2-oxocaprylate and the corresponding ethyl, propyl, isopropyl, butyl, isobutyl, sec.-butyl and tert.-butyl esters; dimethyl, diethyl, dipropyl, diisopropyl, dibutyl, diisobutyl, di-sec.-butyl and di-tert.-butyl mesoxalate, 2-oxosuccinate, 2-oxoglutarate, 2-oxoadipate and 2-oxopimelate; corresponding monoesters or diester of the 2-formyl-, 2-(2'-oxoethyl)- and 2-(3'-oxopropyl)-compounds homologous in respect of the oxo group, and the 2-methyl-, 2-ethyl-, 2-propyl-, 2-isopropyl-, 2-butyl-, 2-isobutyl- and 2-tert.-butyl- compounds corresponding to these homologs; analogous carbonyl compounds which instead of the ester group bear a 1,3-dioxol-2-yl, 1,3-diox-2-yl, 2-methyl-1,3-dioxol-2-yl, 2-ethyl-1,3-dioxol-2yl, 2-propyl-1,3-dioxol-2-yl, 2-methyl-1,3-diox-2-yl, 2-ethyl-1,3-diox-2-yl or 2-propyl-1,3-diox-2-yl group; 2-formyl-, 2-(2'-oxoethyl)- and 2-(3'-oxopropyl)-1,3-dioxolane, 2-formyl-1,3-dioxane, 2-(2'-oxoethyl)-1,3-dioxane and 2-(3'-oxopropyl)-1,3-dioxane, and corresponding 2-methyl, 2-ethyl, 2-propyl, 2-isopropyl, 2-butyl, 2-isobutyl, 2-sec.-butyl and 2-tert.-butyl homologs.

In general, the first step of the reaction is carried out at from 40° to 200° C., preferably from 50° to 100° C., under atmospheric or superatmospheric pressure, continuously or batchwise. Advantageously, solvents which are inert under the reaction conditions are used. Example of suitable solvents are aromatic hydrocarbons, eg. toluene, ethylbenzene, o-, m- and p-xylene, isopropylbenzene and methylnaphthalene; aliphatic and cycloaliphatic hydrocarbons, eg. heptane, pinane, nonane, gasoline factions having a boiling range of from 70° to 190° C., cyclohexane, methylcyclohexane, decalin, hexane, light naphtha, 2,2,4-trimethylpentane, 2,2,3-trimethylpentane, 2,3,3-trimethylpentane and octane, and appropriate mixtures. Advantageously, the solvent is used in an amount of from 150 to 10,000 percent by weight, preferably from 300 to 600 percent by weight, based on starting material II.

The reaction may be carried out as follows: a mixture of the starting materials II and III and the solvent is kept at the reaction temperature for from 2 to 5.5 hours. Advantageously, the water formed is removed continuously whilst the reaction is still proceeding, for example by azeotropic distillation with a suitable solvent, eg. cyclohexane. Thereafter the Schiff base can be isolated from the mixture in the conventional manner, for example by fractional distillation, and the second step of the reaction can be carried out with the isolated, purified base. However, as a rule this procedure will not be chosen, if only for economic reasons; instead it is advantageous to distil off the solvent after the first reaction step, add a solvent suitable for the second step and carry out the second reaction step at the appropriate reaction temperature.

The second reaction step is as a rule carried out at from 0° to 250° C., preferably from 40° to 190° C., under atmospheric or superatmospheric pressure, continuously or batchwise. Advantageously, a solvent which is inert under the reaction conditions is used, such as an alkanol or cycloalkanol, eg. n-butanol, isobutanol, tert.-butanol, glycol, glycerol, n-propanol, isopropanol, amyl alcohol, cyclohexanol, 2-methyl-4-pentanol, ethylene glycol monoethyl ether, 2-ethyl-hexanol, methylglycol and especially ethanol or methanol; a cyclic ether, eg. tetrahydrofuran or dioxane, or one of the solvents already mentioned for the first reaction step. Preferably, the amounts of solvent already mentioned for the first reaction step are used.

The reaction is carried out in the presence of hydrogen, advantageously in excess, in general in an amount of from 3 to 25, preferably from 3 to 50, mole percent, based on starting material II. It is possible to feed hydrogen to the reaction continuously or intermittently and/or to recharge the catalyst itself with hydrogen after a certain reaction time. Preferred hydrogenation catalysts are in general one or more metals of atomic number from 24 to 29, as a rule cobalt, copper, manganese and/or nickel catalysts, for example sintered catalysts of these metals. The metals may also be present in the catalyst in the form of their oxides and/or as a mixture with phosphoric acid.

Advantageous catalysts of the above type contain from 3 to 30 percent by weight of copper, from 0.5 to 10 percent by weight of manganese and from 10 to 80 percent by weight of cobalt or nickel. In addition, from 0.1 to 5 percent by weight of phosphoric acid, based on the amount of metal, may be present. As a rule, the amount of hydrogenation catalyst used for the reaction is from 5 to 30 percent by weight, based on starting material II. The catalyst may be employed as a mixture with a carrier suitable for the reaction, for example silica, in which case the amount of the catalyst is advantageously from 10 to 40 percent by weight of the mixture of catalyst and carrier. As a rule, the amounts of hydrogen fed to the reaction mixture initially and in the course of the reaction are such that at the reaction temperature the reaction pressure always assumes an appropriate value, advantageously from 150 to 300 bar.

The reaction is in general carried out at from 22° to 200° C., preferably from 25° to 160° C., batchwise or continuously. Inert gases, eg. nitrogen, may also be used to bring the pressure to the appropriate value.

It is also advantageous to use copper chromite catalysts, for example appropriate copper/chromium oxide catalysts, such as the copper chromites used by H. Adkins. For example, they contain a copper-chromium spinel ($CuCr_2O_4$) or an oxide mixture in the ratio of $5CuO:4Cr_2O_3$, or are based on such compounds and may contain other oxides also, in the main those of the alkaline earth metals, eg. barium, calcium or magnesium. The copper chromite can advantageously be prepared by precipitating copper ammonium chromate from copper nitrate and ammonium chromate solutions, decomposing the copper ammonium chromate at an elevated temperature and treating the resulting copper chromite with 10 percent strength acetic acid (to dissolve out excess copper oxide). It is also possible to decompose the copper ammonium chromate at a low temperature and to reduce the copper chromite in methanol by means of hydrogen under 100–200 bar. Regarding the preparation of copper chromite catalysts, reference may be made to Houben-Weyl, loc. cit., Volume 4/2, pages 180–183 and to Journal of Applied Chemistry, 5 (1955), 289–295. In general, the process according to the invention is carried out in the presence of copper chromite catalysts at from 22° to 200° C., preferably from 90° to 190° C., batchwise or continuously, under pressure, advantageously under from 50 to 300, especially from 140 to 280, bar.

Other advantageous catalysts are cobalt and nickel sintered catalysts which may contain up to 30 percent by weight of copper, manganese, iron and/or chromium; Raney nickel and Raney cobalt are preferred. Such hydrogenation catalysts are as a rule added in an amount of from 0.5 to 50 percent by weight, based on starting material II. The reaction takes place under a pressure of from 50 to 300 bar, continuously or batchwise; appropriate reaction temperatures are those mentioned above.

The reaction can also be carried out in the presence of palladium and/or its compounds, in general in an amount of from 0.01 to 5 percent by weight, preferably from 0.1 to 2 percent by weight, based on starting material II, of palladium as a finely divided metal, and/or in the form of a finely divided compound thereof, with the above amounts relating to the calculated equivalent amount of palladium. For example, palladium black, palladium powder, palladium bromide, arsenide, cyanide, chloride, nitrate, iodide, oxide, sulfide or sulfate, or complex salts, eg. tetrachloropalladates, tetraamine- or diamine-palladium chlorides and hexachloropalladates may be used as isomerization catalysts. It is also advantageous to apply the said catalysts by conventional methods to carriers, for example active charcoal, barium sulfate, silica gel or zeolites, and to use such supported catalysts for the isomerization. The preparation of such supported catalysts may be effected by any appropriate method, for example by impregnating the carrier with appropriate solutions of the palladium salts, by kneading or by mixing, accompanied by milling, of the components. For details of the preparation of catalysts, especially supported catalysts, reference may be made to Houben-Weyl, Methoden der Organischen Chemie, Volume 4/2, pages 137 et seq. Platinum and/or its compounds, for example platinum oxide, may similarly be used as hydrogenation catalysts. The reaction is carried out with hydrogen, advantageously in an amount of from 1 to 50, preferably from 5 to 25, mole percent, based on starting material II. The hydrogen may be fed to the reaction continuously or intermittently and/or the catalyst itself may be recharged with hydrogen after a certain reaction time. As a rule, the starting material II is reacted at from 20° to 200° C., preferably from 50° to 150° C., under atmospheric or superatmospheric pressure, for example at from 10 to 100 bar.

The second reaction step may be carried out as follows: the solvent is introduced into the reactor which contains the reaction mixture which has been freed from the solvent used in the first step, the hydrogenation catalyst is added and the reaction space is flushed with nitrogen. Hydrogen is then forced in up to the reaction pressure mentioned above. The reaction mixture is then brought to the above temperature and is kept thereat, whilst continuing to introduce hydrogen, until no further hydrogen is consumed by the reaction; in general, this reaction time is from 2 to 8 hours, advantageously from 4 to 12 hours at a lower temperature and from 2 to 6 hours at a higher temperature. The reaction mixture is then cooled and filtered. The end product is isolated from the filtrate by conventional methods, for example by evaporating the filtrate.

In a preferred embodiment, the reaction is carried out as a one-vessel process, by carrying out the first reaction step in the above manner at the reaction temperature of the first step, adding the hydrogenation catalyst and carrying out the second reaction step, if appropriate whilst raising the temperature.

The compounds obtainable by the process of the invention are valuable starting materials for the preparation of dyes and pesticides. In particular, they can be converted, by acylating the nitrogen, into N-substituted compounds which are active compounds for combating phytopathogenic fungi and bacteria. These N-acyl compounds possess both a preventive and a curative action against phytopathogenic fungi on crop plants, for example cereals, Indian corn, rice, vegetables, sugar beet, soybean and peanuts, on fruit trees and ornamental plants and especially on vines, hops, Cucurbitaceae (cucumbers, marrows and melons) and Solanaceae, such as potatoes, tobacco and tomatoes.

Using these active compounds, fungi occurring on plants or on parts of plants (fruit, blossom, leaves, stems, bulbs or roots) can be repressed or destroyed, so that even the subsequent additional growth of the treated plant remains free from such fungi. The active compounds can also be used for the treatment of seed-like material (fruit, bulbs and grain) and of plant seedlings, in order to protect these against fungal infections. In this context, reference may be made to German Laid-Open Applications Nos. DOS 2,350,944, DOS 2,515,091 DOS 2,515,113, DOS 2,513,730, DOS 2,513,732, DOS 2,513,788 and DOS 2,513,789 and to the uses described therein, as well as to the prior art publications specified above.

In the Examples which follow, parts are by weight.

EXAMPLE 1

In a stirred kettle, 128 parts of ethyl pyruvate are added to 121 parts of 2,6-dimethylaniline in 400 parts of cyclohexane. The mixture is heated at 70° C. for 3.5 hours, during which 18 parts of water are distilled off azeotropically. The cyclohexane is distilled off, 400 parts of tetrahydrofuran and 30 parts of Raney nickel are added, the mixture is passed into a downstream autoclave, the latter is flushed three times with nitrogen, and hydrogen is introduced up to a pressure of 200 bar. After 3 hours, the hydrogen pressure has fallen to 175 bar. It is then again raised to 200 bar, after which the autoclave is heated to 50° C. In the next 3 hours, the pressure drops by 5 bar due to hydrogen being taken up; in total, 2.2 parts of hydrogen are consumed. After letting down the autoclave pressure, removing the nickel by filtration under nitrogen and distilling the filtrate, 208 parts (94% of theory) of ethyl 2-(2',6'-dimethylphenylamino)-propionate of boiling point 101° C./0.3 mbar are obtained.

EXAMPLE 2

The reaction is carried out as described in Example 1, but in one vessel, without addition of tetrahydrofuran and without removal of the cyclohexane. 200 parts (90.5% of theory) of ethyl 2-(2',6'-dimethylphenylamino)-propionate of boiling point 101° C./0.3 mbar are obtained.

EXAMPLES 3 TO 11

The following reactions are carried out similarly to Example 1; the reaction conditions are shown in Tables 1 and 2.

TABLE 1

| | | | | | | | |
|---|---|---|---|---|---|---|---|
| | | | 1st reaction step (preparation of the Schiff base) | | | | |
| Example | Starting material II | Parts of starting material II | Starting material III | Parts of starting material III | Solvent (parts) | Reaction time (hours) | Temperature (°C.) |
| 3 | 2-methyl-6-ethylaniline | 135 | methyl α-formyl-propionate [OCH—CH(CH$_3$)—CO$_2$CH$_3$] | 116 | toluene (300) | 4.5 | 85 |
| 4 | 2-methyl-6-ethylaniline | 216 | methyl 2-formyl-2-methyl-propionate [OCH—C(CH$_3$)$_2$—CO$_2$CH$_3$] | 191 | toluene (500) | 5 | 85 |
| 5 | 2-methyl-6-ethylaniline | 40.5 | 2-methyl-2-formyl-(1,3-dioxolane) | 34.8 | cyclohexane (250) | 5 | 70 |
| 6 | 2-methyl-6-ethylaniline | 58 | (1,3-dioxolane-C(H)—C(CH$_3$)=O) | 81 | toluene (250) | 5.5 | 85 |
| 7 | 2,6-dimethylaniline | 121 | methyl pyruvate | 112 | cyclohexane (400) | 4.5 | 70 |
| 8 | 2,6-dimethylaniline | 121 | methyl pyruvate | 112 | toluene (400) | 4 | 85 |
| 9 | 2-methyl-6-ethylaniline | 135 | methyl pyruvate | 112 | cyclohexane (300) | 5 | 70 |
| 10 | 2-methyl-6-ethylaniline | 135 | ethyl pyruvate | 128 | toluene (300) | 5 | 85 |
| 11 | 2-methyl-6-ethylaniline | 65 | dimethyl mesoxalate | 38 | toluene (150) | 2 | 85 |

TABLE 2

| | | | 2nd reaction step (hydrogenation) | | | | | | |
|---|---|---|---|---|---|---|---|---|---|
| Example | Solvent (parts) | Catalyst (parts) | H$_2$ pressure (bar) | Consumption in parts of H$_2$ | Temperature (°C.) | Time (hours) | End product | Yield in parts (% of theory) | Boiling point (°C.) in mbar |
| 3 | methanol (500) | Raney nickel (30) | 150 | 2 | 110 | 6 | 2-methyl-6-ethyl-C$_6$H$_3$—NH—CH$_2$—CH(CH$_3$)—CO$_2$CH$_3$ | 196(84) | 105–108/0.2 |
| 4 | methanol (300) | Raney nickel (20) | 150 | 3.2 | 90 | 6 | 2-methyl-6-ethyl-C$_6$H$_3$—NH—CH$_2$—C(CH$_3$)$_2$—CO$_2$CH$_3$ | 367(92) | 110–115/0.2 |
| 5 | methanol (100) | CuCr$_2$O$_4$ (10) | 250 | 0.6 | 160 | 6 | 2-methyl-6-ethyl-C$_6$H$_3$—NH—CH$_2$—C(CH$_3$)(1,3-dioxolanyl) | 46.5(66) | 98–99/0.1 |
| 6 | methanol (200) | CuCr$_2$O$_4$ (20) | 250 | 0.8 | 160 | 6 | 2-methyl-6-ethyl-C$_6$H$_3$—NH—CH(CH$_3$)—CH(1,3-dioxolanyl) | 68(72) | 95/0.1 |
| 7 | tetrahydrofuran (400) | Raney nickel (30) | 200 | 2.1 | 25 | 8 | 2,6-dimethyl-C$_6$H$_3$—NH—CH(CH$_3$)—CO$_2$CH$_3$ | 188(91) | 87–89/0.2 |

TABLE 2-continued

| Example | Solvent (parts) | Catalyst (parts) | 2nd reaction step (hydrogenation) | | | | End product | Yield in parts (% of theory) | Boiling point (°C.) in mbar |
| --- | --- | --- | --- | --- | --- | --- | --- | --- | --- |
| | | | $H_2$ pressure (bar) | Consumption in parts of $H_2$ | Temperature (°C.) | Time (hours) | | | |
| 8 | methanol (200) | palladium(5% by weight on active charcoal) (10) | 100 | 2.1 | 70 | 6 | 2,6-dimethylphenyl-NH-CH(CH$_3$)-CO$_2$CH$_3$ | 190(92) | 87-89/0.2 |
| 9 | tetrahydrofuran (400) | Raney nickel (30) | 200 | 2.1 | 30 | 8 | 2-methyl-6-ethylphenyl-NH-CH(CH$_3$)-CO$_2$CH$_3$ | 197(89) | 91-93/0.2 |
| 10 | ethanol (500) | Raney nickel (20) | 150 | 2.1 | 90 | 3 | 2-methyl-6-ethylphenyl-NH-CH(CH$_3$)-CO$_2$C$_2$H$_5$ | 211(90) | 95-97/0.2 |
| 11 | methanol (350) | Raney nickel (10) | 150 | 0.7 | 90 | 4 | 2,6-dimethylphenyl-NH-CH(CO$_2$CH$_3$)$_2$ | 71(90) | 117-119/0.2 |

EXAMPLES 12 TO 14 (USE EXAMPLES)

(a) Preparation of the Acyl Compound 25 parts of methyl 3-(2'-methyl-6'-ethyl-phenylamino)-2,2-dimethyl-propionate for Example 4 are dissolved in 100 parts of toluene and 13 parts of sodium bicarbonate are added. 12 parts of chloroacetyl chloride are then added at 0°-5° C., with vigorous stirring. After stirring for 10 hours at 20° C., the sodium chloride which has separated out is filtered off. The filtrate is extracted three times with 150 parts of water. After distilling off the toluene under 20 mbar, 30.6 parts of methyl N-chloroacetyl-3-(2'-methyl-6'-ethylamino)-2,2-dimethylpropionate remain.

NMR: δ=3.7 ppm (CH$_2$Cl) 2 H; 3.2 ppm (CO$_2$CH$_3$) 3 H.

The end products of Examples 5 and 6 are converted to the acyl compounds by corresponding reactions.

(b) Biological Use

Plastic flowerpots of 300 cm$^3$ capacity were used as culture vessels and loamy sand containing about 1.5 percent of humus was used as the substrate. The seeds of the test plants shown in Table 3 are shallow-sown, separated according to species. Immediately thereafter the surface of the soil is sprayed with the active ingredients as a pre-emergence treatment. For this purpose, the substances are suspended in water as the dispersion medium (2 kg/ha of active ingredient in 3,000 liters of water) and the suspension is sprayed through nozzles which give a fine mist. After the active ingredients have been applied, the pots are lightly sprinkled with water in order to start germination and growth and also simultaneously to activate the active ingredients. The vessels are then covered with transparent plastic covers until the plants have taken root. The cover ensures uniform germination of the test plants and prevents evaporation of volatile substances.

The pots are set up in a greenhouse which is kept at from 15° to 40° C. for 6 weeks. Table 4 shows the active substances, the dosages in kg/ha of active ingredient and the species of test plant. The results are assessed on a scale from 0 to 100, 0 denoting no damage or normal emergence and 100 denoting no germination of the plants or complete destruction of at least the visible parts of the shoots.

TABLE 3

| List of plant names Latin name | Abbreviation in Table | English name |
| --- | --- | --- |
| Arachys hypogaea | Arach. hyp. | peanut (groundnut) |
| Beta vulgaris | Beta vulg. | sugarbeet |
| Bromus spp. | Bromus spp. | brome spp. |
| Digitaria spp. | Digit. spp. | crabgrass |
| Echinochloa crus galli | Echino. c.g. | barnyard grass |
| Cyperus spp. | Cyperus spp. | annual sedges |
| (C. ferax Cyperus difformis) | | (grown from seeds) |
| Glycine max | Glyc max | soybean |
| Triticum aestivum | Tritic. aes | wheat |

TABLE 4

Selective herbicidal action on pre-emergence treatment in a greenhouse

Structure: 2,6-R¹-substituted phenyl-N(R)-C(=O)-CH₂Cl

| Example | Substituents R | R¹ | R¹ | kg/ha of active substance | Beta vulg. | Glyc. max | Tritic. aes. | Bromus spp. | Digit. spp. | Echino. c.g. | Cyperus spp. | Arach. hyp. |
|---|---|---|---|---|---|---|---|---|---|---|---|---|
| 12 | 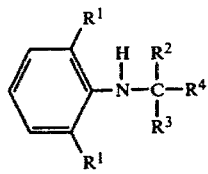 | $C_2H_5$ | $CH_3$ | 2.0 | 0 | 10 | 0 | 90 | 100 | 98 | 100 | 0 |
| 13 | 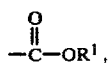 | $CH_3$ | $CH_3$ | 2.0 | 0 | 0 | — | 40 | — | 98 | 100 | 0 |
| 14 | 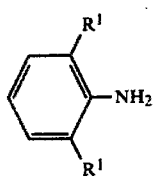 | $C_2H_5$ | $CH_3$ | 2.0 | 0 | — | 0 | — | — | 80 | — | — |
| Comparative Example | 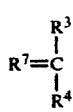 N-isopropyl-chloroacet-anilide | | | 2.0 | 36 | 5 | 42 | 70 | 95 | 89 | 55 | — |

(— means: not tested)

We claim:

1. A process for the preparation of a N-substituted 2,6-dialkylaniline of the formula $$\text{(2,6-R}^1\text{-C}_6\text{H}_3\text{)N(H)-C(R}^2\text{)(R}^3\text{)-R}^4 \quad \text{I}$$

where the individual radicals $R^1$, $R^2$ and $R^3$ may be identical or different and each is alkyl of 1 to 7 carbon atoms, $R^2$ may also be hydrogen, $R^4$ is $$-\underset{\text{O}}{\overset{\|}{C}}-OR^1,$$

where $R^1$ has the above meaning, wherein in a first step a 2,6-dialkylaniline of the formula $$\text{2,6-R}^1\text{-C}_6\text{H}_3\text{-NH}_2 \quad \text{II}$$

where $R^1$ has the above meaning is reacted at a temperature of from 40° to 200° C. with a carbonyl compound of the formula $$R^7=C(R^3)(R^4) \quad \text{III}$$

where $R^3$ and $R^4$ have the above meanings and $R^7$ together with the adjacent carbon atom is $$O=\underset{|}{\overset{|}{C}} \quad \text{or} \quad O=\underset{H}{\overset{|}{C}}-\underset{|}{\overset{|}{C}}-R^2,$$

where $R^2$ has the above meaning, and, after removal of the water formed, in a second step, the resulting Schiff base is hydrogenated with hydrogen in the presence of a hydrogenation catalyst at a temperature of from 0° to 250° C.

2. A process as claimed in claim 1 wherein the reaction is carried out with from 0.8 to 2 moles of starting material III per mole of starting material II.

3. A process as claimed in claim 1, wherein the first reaction step is carried out at from 50° to 100° C.

4. A process as claimed in claim 1, wherein the second reaction step is carried out at from 40° to 190° C.

5. A process as claimed in claim 1, wherein the reaction is carried out using a solvent which is inert under the reaction conditions.

6. A process as claimed in claim 1, wherein the second reaction step is carried out in the presence of hydrogen in an amount of from 3 to 25 mole percent based on starting material II.

7. A process as claimed in claim 1, wherein the second reaction step is carried out using a cobalt, copper, manganese and/or nickel catalyst.

8. A process as claimed in claim 1, wherein the second reaction step is carried out using a copper chromite catalyst.

9. A process as claimed in claim 1, wherein the second reaction step is carried out in the presence of palladium.

* * * * *